US005544382A

United States Patent [19]
Giuliani et al.

[11] Patent Number: 5,544,382
[45] Date of Patent: Aug. 13, 1996

[54] PACING TOOTHBRUSH

[75] Inventors: David Giuliani, Mercer Island; Ryan W. McMahon; David Engel, both of Seattle, all of Wash.

[73] Assignee: Optiva Corp., Bellevue, Wash.

[21] Appl. No.: 306,132

[22] Filed: Sep. 14, 1994

[51] Int. Cl.⁶ .......................... A61C 17/34; A46B 13/02
[52] U.S. Cl. ............................................ 15/22.1; 433/216
[58] Field of Search ................................... 15/22.1, 22.2, 15/22.4, 105, 167.1; 433/216

[56] References Cited

U.S. PATENT DOCUMENTS

| 4,788,734 | 12/1988 | Bauer ................................. 15/105 |
| 5,189,751 | 3/1993 | Giuliani et al. ...................... 15/22.1 |

FOREIGN PATENT DOCUMENTS

| 0435329 | 7/1991 | European Pat. Off. ............. 15/22.1 |
| 2918806 | 11/1980 | Germany ............................ 15/105 |
| 3309687 | 9/1984 | Germany ............................ 15/105 |
| 2097663 | 11/1982 | United Kingdom ................. 15/22.1 |
| 2252234 | 8/1992 | United Kingdom ................. 15/105 |

*Primary Examiner*—Edward L. Roberts, Jr.
*Attorney, Agent, or Firm*—Jensen & Puntigam P S

[57] ABSTRACT

A vibrating toothbrush, which includes a handle member, an elongated arm which has a brushhead at the distal end thereof, and a drive assembly for moving the brushhead at a selected velocity. Responsive to an on/off switch on the toothbrush is an on/off variable, which enables a master clock to produce a drive signal, the on/off variable being reset by a 120-second timer. A quadtimer variable, when in the enabled state, is responsive to the on/off switch to produce an audible signal and a difference in brush velocity at 30-second intervals within the 120-second period.

11 Claims, 3 Drawing Sheets

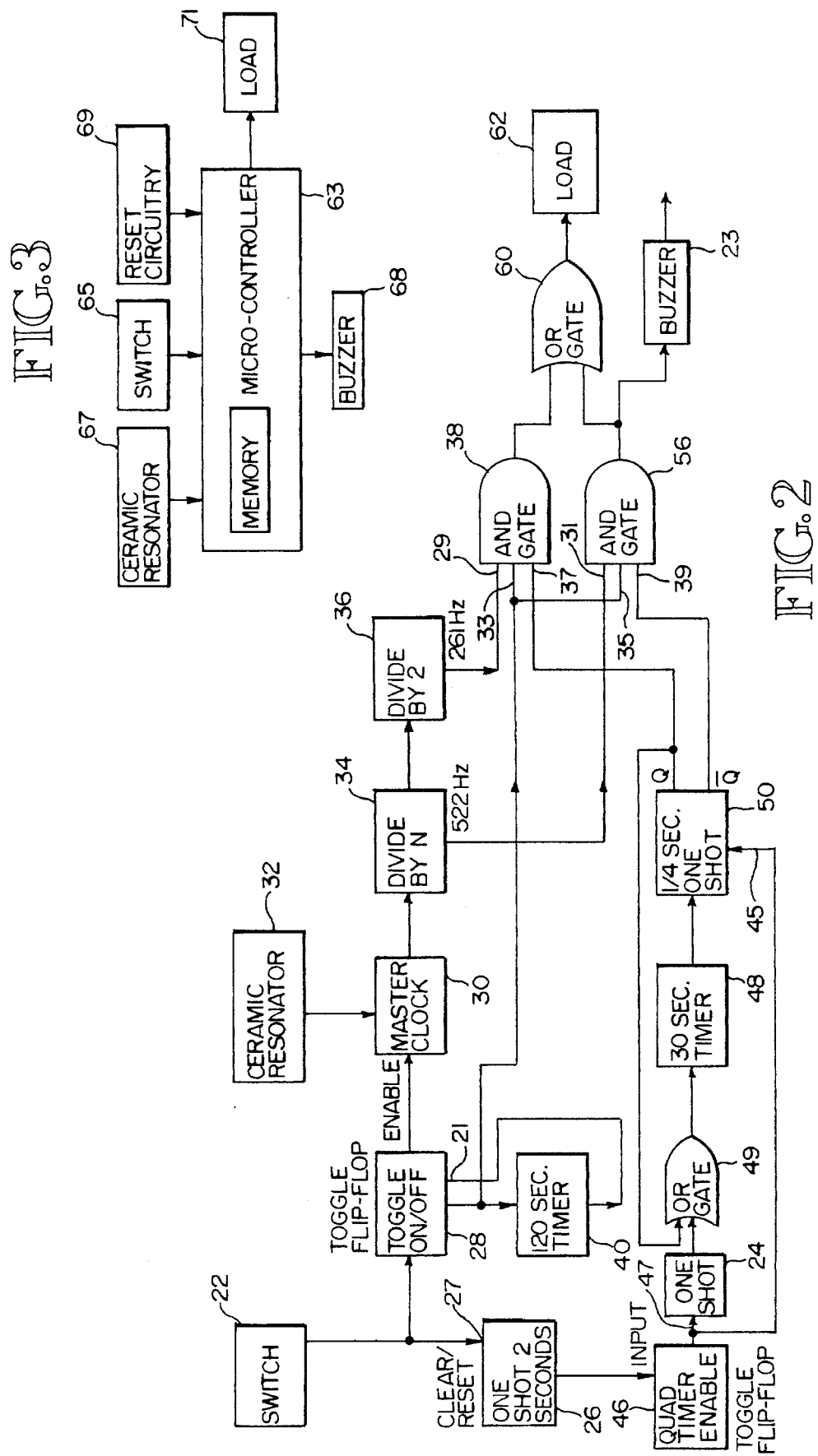

5,544,382

PACING TOOTHBRUSH

TECHNICAL FIELD

This invention relates generally to the art of toothbrushes, and more specifically concerns a power toothbrush which is capable of indicating the passage of selected intervals of time within a longer set time period.

BACKGROUND OF THE INVENTION

Studies have shown that dental hygiene is often uneven, i.e. some areas of the dentition (dental areas) receive more hygiene attention than others. For instance, the posterior (rear) teeth are typically less well cleaned. This is often true even for those patients who generally practice good dental hygiene. While the reasons for an uneven dental condition in a given person's mouth are not fully known, it is believed that differences in the respective times of brushing for the various dental areas is a significant factor. While there has been some effort to provide an indication of the passage of a desired total elapsed time of brushing, which is now regarded to be approximately two minutes, such as by providing a sound at the end of such a total elapsed time, as shown in U.S. Pat. No. 4,788,734, such an approach does not solve the uneven dental condition problem. Hence, it would be desirable to provide further assistance to the user which would tend to promote a good, even dental condition in all areas of the mouth, i.e. uniform cleaning of all teeth.

SUMMARY OF THE INVENTION

Accordingly, the present invention includes a power toothbrush, which includes a support member having a brushhead at a distal end thereof and means for driving the brushhead, and further including a timing means, responsive to the device being turned on, for producing successive indications of intervals of elapsed time, wherein the intervals of elapsed time are related to desired times for brushing portions of the dental region.

BRIEF DESCRIPTION OF THE DRAWINGS

FIG. 2 is a circuit diagram showing a hardware implementation of the present invention.

FIG. 3 is a block diagram showing a software implementation of the present invention.

BEST MODE FOR CARRYING OUT THE INVENTION

Figure 1:
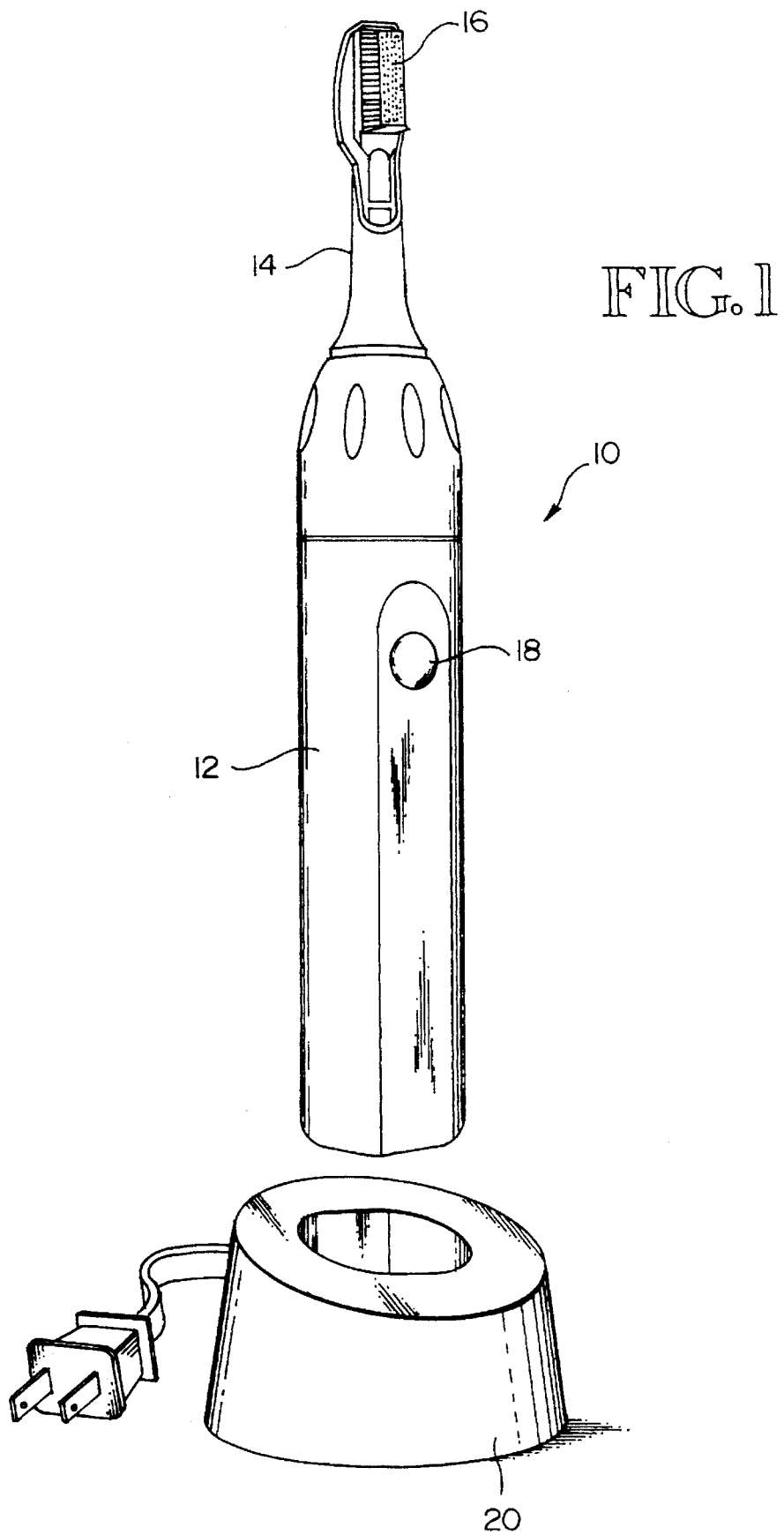
FIG. 1 is a perspective view of the toothbrush of the present invention.

FIG. 1 shows an exterior view of a power toothbrush which incorporates the present invention. Such a power toothbrush could be designed to produce any one of various brushing actions, including back and forth, side to side, rotational, and others. The toothbrush 10 includes a handle 12, an elongated arm 14 which is vibrated or otherwise activated by a driving assembly (not shown) in handle 12, and a brushhead 16 at the distal end of arm 14. While the toothbrush shown in FIG. 1 and briefly described herein is driven electromagnetically, it should be understood that other means, including electromechanical and mechanical, can be used to drive arm 14 and hence brushhead 16, since the principles of the present invention are not dependent upon an electromagnetic driver.

The toothbrush 10 is operated by a button switch 18 which is pushed and released by the operator, the switch thus having two operating positions. When not in use, the electromagnetic toothbrush sits in a base unit 20, which is a charge unit for a rechargeable battery present in handle 12. Hence, there is no direct connection between the toothbrush and an exterior source of electrical energy (such as a cord to a wall plug) when the toothbrush is removed from the base and put into use.

U.S. Pat. No. 5,189,751, entitled "Vibrating Toothbrush Using A Magnetic Driver", which is assigned to the same assignee as that of the present invention, discloses an electromagnetic toothbrush which drives a brushhead at a frequency in the range of 150–400 Hz, although it should be understood that the principles of the present invention are not limited to a particular brushhead frequency. The contents of the '751 patent are hereby incorporated by reference.

In the vibrating toothbrush shown in the '751 patent, switch 18 is used to enable a master clock, the signal from which is then divided down to a desired number, which divided signal is then applied to the electromagnetic circuit, which in turn drives a brushhead at the distal end of the arm. The toothbrush of the present invention is similar to the toothbrush described in the '751 patent, but includes a particular timing capability, so that the user may conveniently "pace" his or her brushing time within a given set time. Specifically, the toothbrush is designed to provide a signal at specified times within an overall set operating time, such as, for instance, two minutes.

As stated above, it is known for a toothbrush to provide an indication of total desired elapsed time. In the commercial implementation of the toothbrush disclosed in the '751 patent, for instance, a 120-second timer is used, and operation of the toothbrush hence stops after 120 seconds from the initiation of switch 18 by the user. Such a toothbrush thus provides a reliable indication of a total elapsed time which has been deemed appropriate for brushing.

In originating the present invention, and attempting to address the problem of uneven dental condition noted above, the inventors determined that brushing time alone, even apart from the technique of brushing, was a major factor in producing uniform results for all the dental areas of the mouth. Hence, it was determined that providing a pacing indication within a total set time of two minutes, which would permit a user to pace the use of the toothbrush area by area within the mouth, would likely be helpful in producing uniform dental hygiene results. The inventors further determined, after some study and evaluation, that the most productive time/area division was four identical time intervals, hence in effect dividing brushing time between four quadrants of the mouth. It was believed that this would provide a reliable and useful pace of brushing to provide the even brushing effect desired.

FIG. 2 shows a hardware circuit embodiment designed to accomplish the desired time division. Switch 22, as indicated previously, has two conditions. When the switch is depressed by the user and maintained in that position, the output from switch 22 is "low" (logic 0), while when the switch is released, the output is "high" (logic 1). When the output from switch 22 is high, a one-shot multivibrator 26 with a two-second time period is cleared by the signal at input 27. When the switch is depressed, however, the resulting low signal has two effects. First, multivibrator 26 is reset and begins to count down for two seconds (if switch held depressed). Second, "toggle" flip-flop 28 changes state (from "off" to "on" or vice versa).

Flip-flop 28 thus controls the on/off condition of the apparatus When it is toggled to "on," it will enable master clock 30 to begin producing a signal output of selected frequency. The frequency of the output from master clock 30 is controlled by a stable frequency source, such as a ceramic resonator 32, which could alternatively be a crystal or other oscillator circuit capable of providing the desired stable frequency. In the present invention, the frequency of the master clock signal is divided by frequency divider 34 to produce a frequency of 522 Hz. The 522 Hz signal is then applied to input 31 of AND gate 56 and to another divider 36, which reduces the frequency to 261 Hz. The out of divider 36 is applied to input 29 of AND gate 38.

The output from toggle flip-flop 28 is also applied to a 120-second timer 40, which immediately begins timing down. At the end of the 120-second interval, an output is produced which is applied to a reset pin 21 of flip-flop 28, which toggles it to an "off" condition. Timer 40 thus provides the basic full on time (set time interval) for the operation of the toothbrush.

The output from flip-flop 28 is also applied as an input to both AND gate 38 (input 33) and AND gate 56 (input 35) A "false" or "low", i.e. "off", condition of flip-flop 28 thus prevents divided clock signals from being applied to OR gate 60 (and then to the load) through either AND gate. Conversely, when flip-flop 28 is "true", i.e. "on", and timer 40 is counting down, a high signal is applied to input 33 of AND gate 38 and input 35 of AND gate 56, while a 522 Hz signal is applied to input 31 of AND gate 56 and a 261 Hz signal is applied to input 29 of AND gate 38.

The one-shot two-second multivibrator 26 is responsive to switch 22 as follows. If switch 22 is held depressed for more than two seconds, one-shot 26 produces an output signal which is applied to a toggle flip-flop 46, similar to toggle flip-flop 28, reversing its previous state, from "enabled" to "disabled" or vice versa. Once flip-flop 46 indicates quad timer enable by a two-second hold of switch 22, it will remain in the "enabled" state until the next successive two-second hold of switch 22. The output from flip-flop 46 is applied to the reset pin 45 of a ¼-second one-shot 50, and to the trigger input of a one-shot 24, the output of which is a short duration high signal (usually less than 1 msec) applied to OR gate 49, the output of which triggers a 30-second timer 48 which, as can be seen, is exactly one-fourth of the overall desired set time (120 seconds) for brushing. When 30-second timer 48 runs out, a signal is applied to a ¼-second one-shot circuit 50. The Q output of one-shot 50 is applied back as an input to OR gate 49, thereby triggering a subsequent 30-second time period, ¼ second after termination of the immediately prior 30-second time period, as clarified below. This provides the desired repetitive time period.

When the output of toggle flip-flop 46 indicates quad timer disabled, the ¼-second one-shot 50 is reset by a signal at input 45, which prevents the ¼-second interrupts of the 261 Hz signal applied to OR gate 60 through AND gate 38.

Output Q of one-shot 50 is "true", i.e. high, during the entire time of toothbrush operation, other than the ¼-second period; output $\overline{Q}$ is "true", i.e. high, when Q is not true, i.e. low. Outputs Q and $\overline{Q}$ are applied, respectively, at inputs 37 and 39 to AND gates 38 and 56. Outputs Q and $\overline{Q}$ in effect thus determine which of the two AND gates 38, 56 conducts clock signals from the other input lines to those AND gates from the frequency counters 36, 34, respectively, and then to OR gate 60. Neither AND gate produces an output unless toggle flip-flop 28 is "on". If it is, then either a 261 Hz signal from divider 36 or a 522 Hz signal from divider 34 is conducted to OR gate 60 and then to the load 62, depending on whether output Q or output $\overline{Q}$ is true. In typical operation of the pacing toothbrush, the load 62 thus will receive a 261 Hz signal for 30 seconds, followed by a 522 Hz signal for ¼ second. This sequence continues until the 120-second timer times out.

During the periodic ¼-second intervals, two significant effects occur. First, the 522 Hz signal is sufficiently fast to produce a "null" effect at the brushhead (the load contact with the user), which is hence immediately distinguishable by the user. Also, the 522-Hz signal is used to produce a ¼-second beep. The user hence knows both aurally and tactilely that a 30-second time interval has elapsed. Various methods of producing the desired beeps can be used. For instance, a piezoelectric buzzer 23 could be connected to the output of AND gate 56, so that an alternating pulse is applied during the ¼-second interval, creating an audible beep. An alternative is to interrupt the driver with a silence "burst". Each 30-second interval represents the time the user should be taking for each quadrant of dentition (dental areas) in the mouth. Hence, the user will successively progress from, for instance, the upper left quadrant to the upper right quadrant, then to the lower right and the lower left, both inner and outer sides of the teeth as well as the upper surfaces thereof. Other sequences, of course, can be used.

The user now, however, has information by which the brushing can be paced to produce a uniform dental hygiene condition. It should be understood that other sets of intervals can be used, although four was experimentally determined to be a good compromise between an overly complex arrangement (i.e. eight time intervals) and a very simple arrangement (i.e. two intervals), which is not likely to produce an even effect.

Figure 4:
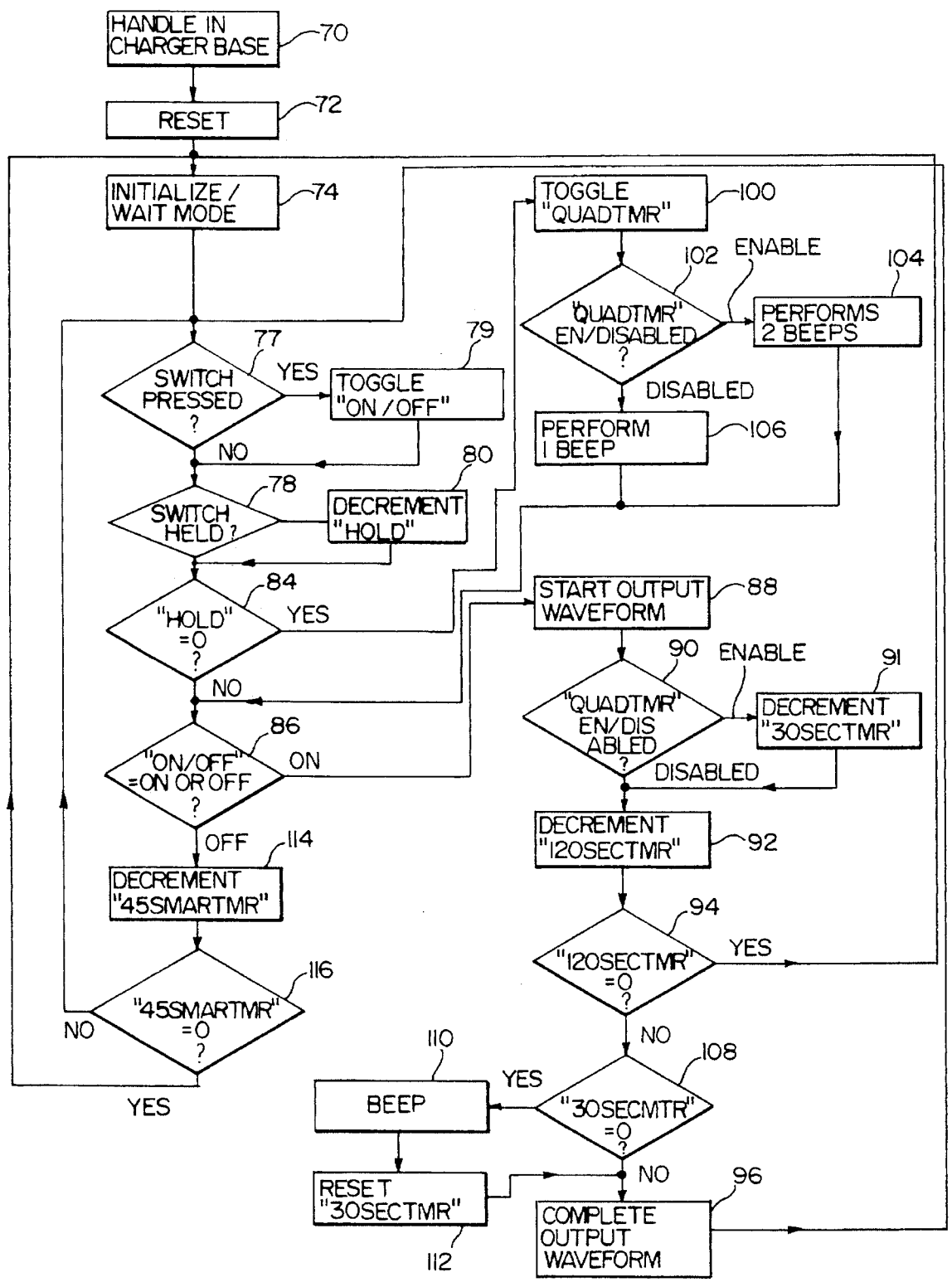
FIG. 4 is a flow chart for the software implementation of FIG. 3.

A software implementation of the present invention is shown in FIGS. 3 and 4. This embodiment includes a microprocessor controller 63, a control switch 65, a ceramic resonator 67, and reset circuitry 69. The software embodiment operates into a load 71 which comprises two driving transistors and a center tapped coil, which in turn results in brushhead movement in an electromagnetic driving system. Switch 65 is used to turn the apparatus on and off, while the ceramic resonator 67 is used to determine the clock frequency of the microprocessor controller. The reset circuitry produces a reset signal to the software in the microprocessor when the unit is placed in the charger base.

The operation of the software embodiment is perhaps best understood by describing the four possible operating states of the toothbrush. In a first operating state, the toothbrush is positioned in charger base unit 20. This is represented by block 70 in FIG. 4. In this state, a reset command is initiated, as shown by block 72, and the software is initialized, as shown at block 74, at the conclusion of which the software enters a wait mode. The software then in effect waits for switch 65 to be pressed by a user.

The remaining three operating states occur when the toothbrush has been removed from base unit 20. In these three states, the condition of the button switch 65 (18 in FIG. 1) is monitored by the software, as shown by block 77. The monitoring function, which results in a cycling through of the flow chart, occurs at a high rate, approximately 2 MHz. When the switch 65 is pressed, an on/off variable in the software indicating the operating condition of the unit is toggled (from off to on or vice versa), as shown at block 79. Thus, when the toothbrush is off, and the switch is then pressed, the on/off variable is toggled to on. This is a second operating state. A determination is then made whether the switch 65 is held for 2 seconds, as shown by blocks 78, 80 and 84. If yes, then a quadtimer variable is toggled, at block 100. If the quadtimer variable was previously in an enabled state, then it would change to disabled and vice versa. The quadtimer variable and following software functions control the pacing feature of the toothbrush.

A determination of the new state of the quadtimer variable is made after the quadtimer variable has changed state, as shown at block 102. If the switch 65 has been pushed for 2 seconds, so that the state of the quadtimer variable changes, 2 beeps are produced if the quadtimer is now enabled (block 104), while 1 beep is produced if the quadtimer is now disabled (block 106). Beeps may be produced by changing the drive frequency applied to the load, e.g. from 261 Hz to 522 Hz, or by other techniques, such as interrupting the drive signal, or using a piezoelectric buzzer 68 connected to the microcontroller, or a combination thereof. Hence, the user knows whether or not the pacing feature is enabled or disabled following the pressing of the switch for 2 seconds. The quadtimer variable will then remain in that state until the next 2-second pressing of the switch.

In each cycle through the software, regardless of the status of the quadtimer variable, the condition of the on/off variable is determined, as shown by block 86. In the "on" state (the second operating condition), the output signal is started, as shown at block 88, to drive the load. If the quadtimer is enabled, a 30-second decrementing timing function is begun, as shown at block 91. A 120-second decrementing time function begins (block 92) as soon as the unit is turned on. When the 30-second timing function goes to zero, within the 120-second timing period, as shown at blocks 94 and 108, a beep will be produced as shown at block 110, and the 30-second timing function will be reset, as shown at block 112. During this time, the output signal is applied to the load.

When the 120-second timing function is recognized to be at zero, as shown by block 94, the software is then initialized and returns to the wait mode (block 74). The established set period for brushing is now over. When the switch 65 is again pushed, the output signal to drive the load begins again, with the quadtimer variable being in the same status, unless the switch is held for longer than two seconds.

In a third operating state, button switch 65 is turned off by the user less than 120 seconds after it has been initially turned on. Block 86 now indicates that the on/off toggle 79 is "off", so that no output signals are produced. When the on/off variable (block 79) is toggled to off, a 45-second timing function is initiated, shown at block 114. When this goes to zero, as shown at block 116, the software is initialized and set to the wait mode, at block 74.

In a fourth state, which is a variation of the third state, the toothbrush is turned back on again within a 45-second period after it has been turned off. Since the software has not been initialized in that time, the software (i.e. the 30-second and 120-second timing functions) picks up where it was when the unit was turned off. The on condition of the on/off variable 79 is recognized, at block 86, and the output driving waveforms begin again, until the 120-second function goes to zero. Hence, when the toothbrush is turned on and then turned off within 120 seconds, the software in effect remains in a "halt" condition thereafter for 45 seconds, before the software is initialized and reset.

Hence, a vibrating toothbrush has been disclosed which includes a capability of providing an indication to the user of certain elapsed periods of time within an overall set timer, which are related to optimal times for cleaning one portion of the dental region.

Although a preferred embodiment of the invention has been disclosed herein for illustration, it should be understood that various changes, modifications and substitutions may be incorporated in such embodiment without departing from the spirit of the invention, which is defined by the claims which follow:

What is claimed is:

1. A dental hygiene device for cleaning teeth, comprising:
    a power toothbrush, including a support member having a brushhead at a distal end thereof and means for driving the brushhead;
    timing means, responsive to the device being turned on, for producing successive indications of intervals of elapsed time, wherein the intervals of elapsed time are related to desired times for brushing portions of the dental region, wherein the successive indications of time are provided within a pre-established set period of time during which the brush is operating; and
    means for maintaining the status of the timing means for a selected period of time after the apparatus has been turned off during said pre-established period of time after the apparatus has been turned on.

2. An apparatus of claim 1, wherein the successive indications of time are provided within a preestablished set period of time during which the toothbrush is operating.

3. An apparatus of claim 2, wherein the set period of time is approximately two minutes and wherein the selected intervals of time are approximately 30 seconds.

4. An apparatus of claim 1, wherein the indications are a selected one of a) an audible signal and b) a detectable change in bristle movement.

5. An apparatus of claim 4, wherein the indications comprise both an audible signal and a detectable change in bristle movement.

6. An apparatus of claim 1, including means for changing the state of the timing means between enabled and disabled after the apparatus is turned on.

7. An apparatus of claim 6, wherein the changing means is responsive to an on/off switch being pressed on for a selected period of time.

8. An apparatus of claim 7, wherein the selected period of time is approximately two seconds.

9. An apparatus of claim 6, wherein a first audible signal indicates that the timing means has been enabled and a second audible signal different from the first audible signal indicates that the timing means has not been activated.

10. A dental hygiene device for cleaning teeth, comprising:
    a power toothbrush, including a support member having a brushhead at a distal end thereof and means for driving the brushhead;
    timing means, responsive to the device being turned on, for producing successive indications of intervals of elapsed time, wherein the intervals of elapsed time are related to desired times for brushing portions of the dental region; and
    means for changing the state of the timing means between enabled and disabled after the device has been turned on without turning the device off.

11. An apparatus of claim 10, wherein said changing means is responsive to a device on/off switch being held on for a selected period of time.

\* \* \* \* \*